United States Patent
Irazabal Mira et al.

(10) Patent No.: US 12,042,266 B2
(45) Date of Patent: Jul. 23, 2024

(54) SYSTEM AND METHOD FOR CLASSIFYING AUTOSOMAL DOMINANT POLYCYSTIC KIDNEY DISEASE PATIENTS

(71) Applicant: MAYO FOUNDATION FOR MEDICAL EDUCATION AND RESEARCH, Rochester, MN (US)

(72) Inventors: Maria V. Irazabal Mira, Rochester, MN (US); Vicente E. Torres, Rochester, MN (US); Peter C. Harris, Rochester, MN (US); Laureano J. Rangel Latuche, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 890 days.

(21) Appl. No.: 16/981,609

(22) PCT Filed: Mar. 14, 2019

(86) PCT No.: PCT/US2019/022328
§ 371 (c)(1),
(2) Date: Sep. 16, 2020

(87) PCT Pub. No.: WO2019/178394
PCT Pub. Date: Sep. 19, 2019

(65) Prior Publication Data
US 2021/0045659 A1    Feb. 18, 2021

Related U.S. Application Data

(60) Provisional application No. 62/644,027, filed on Mar. 16, 2018.

(51) Int. Cl.
*A61B 5/107*     (2006.01)
*A61B 5/00*      (2006.01)
(Continued)

(52) U.S. Cl.
CPC .......... *A61B 5/1073* (2013.01); *A61B 5/055* (2013.01); *A61B 5/1075* (2013.01);
(Continued)

(58) Field of Classification Search
CPC ..... A61B 5/1073; A61B 5/055; A61B 5/1075; A61B 5/4842; A61B 5/7475; A61B 6/032;
(Continued)

(56) References Cited

U.S. PATENT DOCUMENTS

2018/0253849 A1*  9/2018  Bae ..................... G06T 7/12

FOREIGN PATENT DOCUMENTS

WO  2017/048744 A1  3/2017
WO  WO-2017048744 A1 * 3/2017 ........... G06K 9/6207

OTHER PUBLICATIONS

Irazabal et al., "Imaging Classification of Autosomal Dominant Polycystic Kidney Disease: A Simple Model for Selecting Patients for Clinical Trials", Journal American Society of Nephrology, 26: 160-172, 2015 (Year: 2015).*

(Continued)

*Primary Examiner* — Joy Chng
(74) *Attorney, Agent, or Firm* — Daniel J. Chalker; Edwin S. Flores; Chalker Flores, LLP

(57) ABSTRACT

An apparatus and computerized method of classifying a patient that has been previously diagnosed to have autosomal dominant polycystic kidney disease (ADPKD) includes providing a computing device having an input/output interface, one or more processors and a memory; receiving a total kidney volume (TKV), a patient height, and a patient age for the patient via the input/output interface; determining a height adjusted TKV (HtTKV) based on the total kidney volume and the patient height using the one or more processors; determining an ADPKD classification for (Continued)

the patient based on the height adjusted TKV and the patient age using the one or more processors; and providing the ADPKD classification for the patient via the input/output interface.

25 Claims, 11 Drawing Sheets

(51) Int. Cl.

| | |
|---|---|
| *A61B 5/055* | (2006.01) |
| *A61B 6/03* | (2006.01) |
| *G06T 7/62* | (2017.01) |
| *G16H 10/20* | (2018.01) |
| *G16H 10/40* | (2018.01) |
| *G16H 30/20* | (2018.01) |
| *G16H 30/40* | (2018.01) |
| *G16H 40/20* | (2018.01) |
| *G16H 40/67* | (2018.01) |
| *G16H 50/20* | (2018.01) |
| *G16H 50/30* | (2018.01) |
| *G16H 50/50* | (2018.01) |

(52) U.S. Cl.
CPC .......... *A61B 5/4842* (2013.01); *A61B 5/7475* (2013.01); *A61B 6/032* (2013.01); *G06T 7/62* (2017.01); *G16H 10/20* (2018.01); *G16H 10/40* (2018.01); *G16H 30/20* (2018.01); *G16H 30/40* (2018.01); *G16H 40/20* (2018.01); *G16H 40/67* (2018.01); *G16H 50/20* (2018.01); *G16H 50/30* (2018.01); *G16H 50/50* (2018.01); *G06T 2207/10081* (2013.01); *G06T 2207/10088* (2013.01); *G06T 2207/30084* (2013.01)

(58) Field of Classification Search
CPC ......... A61B 5/201; A61B 5/1072; A61B 6/03; A61B 6/52; A61B 2576/02; G06T 7/62; G06T 2207/10081; G06T 2207/10088; G06T 2207/30084; G16H 10/20; G16H 10/40; G16H 30/20; G16H 30/40; G16H 40/20; G16H 40/67; G16H 50/20; G16H 50/30; G16H 50/50
USPC ....................................................... 705/2–3
See application file for complete search history.

(56) References Cited

OTHER PUBLICATIONS

Kline et al., Automatic total kidney volume measurement on follow-up magnetic resonance images to facilitate monitoring of autosomal dominant polycystic kidney disease progression, Nephrol Dial Transplant (2016) 31: 241-248 doi: 10.1093/ndt/gfv314 Advance Access Publication Aug. 31, 2015 (Year: 2015).*

Pet et al., Imaging-Based Diagnosis of Autosomal Dominant Polycystic Kidney Disease, JASN Mar. 2015, 25 (3) 746-753; DOI: https://doi.org/10.681/ASN.2014030297, Published online Feb. 27, 2015 (Year: 2015).*

Chapman et al., Kidney Volume and Functional Outcomes in Autosomal Dominant Polycystic Kidney Disease, Clin J Am Soc Nephrol, Mar. 2012; 7(3): 479-486. doi: 10.2215/CJN.09500911 Published online Mar. 7, 2012 (Year: 2012).*

Chapman et al., "Kidney Volume and Functional Outcomes in Autosomal Dominant Polycystic Kidney Disease", Clinical Journal American Society of Nephrology, vol. 7, 2012, 479-486.

Daftary et al., "A Novel Role of the Sp/KLF Transcription Factor KLF11 in Arresting Progression of Endometriosis", PLOS One, Mar. 2013, vol. 8, Issue 3.

Gansevoort et al., "Recommendations for the use of tolvaptan in autosomal dominant polycystic kidney disease: a position statement on behalf of the ERA-EDTA Working Groups on Inherited Kidney Disorders and European Renal Best Practice", Nephrol Dial Transplant (2016) 31: 337-348.

Irazabal et al., "Imaging Classification of Autosomal Dominant Polycystic Kidney Disease: A Simple Model for Selecting Patients for Clinical Trials", Journal American Society of Nephrology, 26: 160-172, 2015.

Irazabal et al., "Prognostic enrichment design in clinical trials for autosomal dominant polycystic kidney disease: the HALT-PKD clinical trial", Nephrol Dial Transplant (2016) 0: 1-9.

Irazabal et al., "Prognostic Enrichment Design in Clinical Trials for Autosomal Dominant Polycystic Kidney Disease: The TEMPO 3:4 Clinical Trial", Kidney International Reports (2016) 1, 213-220.

Kline et al., "Automatic total kidney volume measurement on follow-up magnetic resonance images to facilitate monitoring of autosomal dominant polycystic kidney disease progression", Nephrol Dial Transplant, (2016) 31: 241-248.

Pei et al., "Imaging-Based Diagnosis of Autosomal Dominant Polycystic Kidney Disease", Journal American Society of Nephrology, 2015, 26: 746-753.

International Search Report, PCT/US2019/022328, Australian Patent Office, Jun. 11, 2019.

* cited by examiner

FIG. 4C

Input screen box 3 & 4

3 — ADPKD Classification if Kidney Volume previously calculated by Stereology

Required Data Entry
- Kidney Volume (mL): 757.5
- Patient Height (m): 1.7
- Patient Age (years): 25

[Clear All]

Calculated Results
- Height Adjusted TKV (mL/m): [ ]
- ADPKD Classification: [ ]

[Calculate Classification]

4 — Prediction of Future eGFR based on Classification

Required Data Entry
- Serum Creatinine (mg/dL)†: 1.2
- Age (years): 25
- Race (AA/O)‡: O
- Gender (M/F): M
- ADPKD Classification: 1C
- Future time (years): 5

[Clear All]

Calculated Results
- Current eGFR (mL/min/1.73m2): [ ]
- Future eGFR (mL/min/1.73m2): [ ]

[Calculate Current and Future eGFR]

† This equation is only valid with creatinine essays that are traceable to IDMS
‡ AA = African American; O = All ethnic groups other than African American

[Chart: HITKV (mL/m) vs age (15–80 years), showing Class 1A, Class 1B, Class 1C, Class 1D, Class 1E regions]

FIG. 4D

Output screen box 3 & 4

3     ADPKD Classification if Kidney Volume previously calculated by Stereology

| Required Data Entry | | Calculated Results | |
|---|---|---|---|
| Kidney Volume (mL) | 757.5 | Height Adjusted TKV (mL/m) | 445.6 |
| Patient Height (m) | 1.7 | | |
| Patient Age (years) | 25 | ADPKD Classification | 1C |
| Clear All | | Calculate Classification | |

4     Prediction of Future eGFR based on Classification

| Required Data Entry | | Calculated Results | |
|---|---|---|---|
| Serum Creatinine (mg/dL)† | 1.2 | | |
| Age (years) | 25 | | |
| Race (AA/O)‡ | O | Current eGFR (mL/min/1.73m2) | 83.5 |
| Gender (M/F) | M | Future eGFR (mL/min/1.73m2) | 72.3 |
| ADPKD Classification | 1C | | |
| Future time (years) | 5 | | |
| Clear All | | Calculate Current and Future eGFR | |

† This equation is only valid with creatinine essays that are traceable to IDMS
‡ AA = African American; O = All ethnic groups other than African American

SYSTEM AND METHOD FOR CLASSIFYING AUTOSOMAL DOMINANT POLYCYSTIC KIDNEY DISEASE PATIENTS

CROSS-REFERENCE TO RELATED APPLICATIONS

This application claims priority to and is a National Stage of International Application No. PCT/US2019/022328 filed on Mar. 14, 2019, which claims priority to U.S. Provisional Patent Application Ser. No. 62/644,027, filed Mar. 16, 2018, entitled "System and Method for Classifying Autosomal Dominant Polycystic Kidney Disease Patients," the contents of each of which is incorporated by reference herein in their entirety.

TECHNICAL FIELD OF THE INVENTION

The present invention relates in general to patient classification, and more particularly, to a system and method for classifying autosomal dominant polycystic kidney disease patients.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with classifying autosomal dominant polycystic kidney disease patients.

Autosomal Dominant Polycystic Kidney Disease (ADPKD) is the fourth leading cause of renal failure among adults in the US and worldwide, affecting approximately 1:500 to 1:1000 live births. However, there is still no FDA-approved therapy for the disease and the exact mechanisms of cystogenesis remain to be elucidated. Cyst development starts in utero and continues through the patient lifetime. Individuals are born with normal renal function that is preserved for several decades and by the time the glomerular filtration rate (GFR) starts to decline, most of the kidneys have been replaced by cysts. The median age of end-stage renal disease (ESRD) is 54 years for PKD1 and 74 years for PKD2, but the rate of disease progression varies widely among individuals. This variability, together with the maintenance of normal GFR until late stages, represents a major challenge for nephrologists following these patients. At an early stage, it is difficult to predict disease progression or evaluate a new therapy based solely on renal function markers. On the other hand, if new therapies are implemented when GFR starts to decline and most irreversible damage has occurred, they are less likely to be effective.

The Consortium for Radiologic Imaging Studies of PKD (CRISP) study [1] has shown that in patients with ADPKD the increase in kidney and cyst volumes directly correlates with GFR decline, underscoring the potential of Total Kidney Volume (TKV) to monitor disease progression and as primary or secondary endpoint in clinical trials for ADPKD. However, TKV has limitations as a surrogate marker for disease progression. Volume measurements for this purpose require high precision and are laborious. Furthermore, TKV does not always predict change in renal function, as for example in patients with few large cysts or in patients with renal atrophy secondary to ischemia or urinary tract obstruction.

In a previous study [2], patients from the Mayo Clinic Translational PKD Center with ADPKD (n=590) with computed tomography/magnetic resonance images and three or more eGFR measurements over ≥6 months were classified radiologically as typical (n=538) or atypical (n=52). Total kidney volume (TKV) was measured using stereology (TKVs) and ellipsoid equation (TKVe). Typical patients were randomly partitioned into development and internal validation sets and subclassified according to height-adjusted TKV (HtTKV) ranges for age (1A-1E, in increasing order). CRISP participants (n=173) were used for external validation. TKVe correlated strongly with TKVs, without systematic underestimation or overestimation. A longitudinal mixed regression model to predict eGFR decline showed that $\log_2$HtTKV and age significantly interacted with time in typical patients, but not in atypical patients. When 1A-1E classifications were used instead of $\log_2$HtTKV, eGFR slopes were significantly different among subclasses and, except for 1A, different from those in healthy kidney donors. The equation derived from the development set predicted eGFR in both validation sets. The frequency of ESRD at 10 years increased from subclass 1A (2.4%) to 1E (66.9%) in the Mayo cohort and from 1C (2.2%) to 1E (22.3%) in the younger CRISP cohort. Class and subclass designations were stable.

The classification of ADPKD patients by prespecified imaging findings is as follows:

Class 1: Typical ADPKD
  Bilateral and diffuse distribution, with mild, moderate, or severe replacement of kidney tissue by cysts, where all cysts contribute similarly to TKV.
Class 2: Atypical APDKD
  A: Unilateral—Diffuse cystic involvement of one kidney causing marked renal enlargement with a normal contralateral kidney defined by a normal kidney volume (<275 ml in men; <244 ml in women) and having no or only 1-2 cysts
    Segmental—Cystic disease involving only one pole of one or both kidneys and sparing the remaining renal tissue.
    Asymmetric—Diffuse cystic involvement of one kidney causing marked renal enlargement with mild segmental or minimal diffuse involvement of the contralateral kidney defined by a small number of cysts (>2 but <10) and volume accounting for <30% of TKV.
    Lopsided—Bilateral distribution of renal cysts with mild replacement of kidney tissue with atypical cysts where ≤5 cysts account for ≥50% TKV (the largest cyst diameter is used to estimate individual cyst volume).
  B: Bilateral presentation with:
    acquired unilateral atrophy—Diffuse cystic involvement of one kidney causing moderate to severe renal enlargement with contralateral acquired atrophy.
    bilateral kidney atrophy—Impaired renal function (serum creatinine≥1.5 mg/dl) without significant enlargement of the kidneys, defined by an average length<14.5 cm, and replacement of kidney tissue by cysts with atrophy of the parenchyma.

Class 1 patients are subclassified based on HtTKV limits, defined as estimated kidney growth rates, for their age as follows:
Class 1A (slow progression): <1.5% estimated kidney growth rate
  Estimated slopes of eGFR loss: −0.23 ml/min per 1.73 m² per year for men
  −0.03 ml/min per 1.73 m² per year for women
Class 1B (intermediate progression): 1.5 to 3.0% estimated kidney growth rate
  Estimated slopes of eGFR loss: −1.33 ml/min per 1.73 m² per year for men
  −1.13 ml/min per 1.73 m² per year for women
Class 1C (rapid progression): 3.0 to 4.5% estimated kidney growth rate
  Estimated slopes of eGFR loss: −2.63 ml/min per 1.73 m² per year for men
  −2.43 ml/min per 1.73 m² per year for women
Class 1D (very rapid progression): 4.5 to 6.0% estimated kidney growth rate
  Estimated slopes of eGFR loss: −3.48 ml/min per 1.73 m² per year for men
  −3.29 ml/min per 1.73 m² per year for women
Class 1E (most rapid progression): >6.0% estimated kidney growth rate
  Estimated slopes of eGFR loss: −4.78 ml/min per 1.73 m² per year for men
  −4.58 ml/min per 1.73 m² per year for women The eGFR was calculated using the Chronic Kidney Disease Epidemiology Collaboration equation [3].

Another study [4], involved patients from the TEMPO 3:4 Trial, a prospective, randomized, double-blinded, controlled clinical trial in adult subjects with ADPKD, an estimated creatinine clearance >60 ml/min and total kidney volume>750 ml. The study was a post hoc exploratory analysis to investigate the performance of the previously developed imaging classification of ADPKD for prognostic enrichment design in clinical trials, where the recommendation was inclusion of only classes 1C to 1E in RCTs.

Due to the entry criteria, the study population of TEMPO 3:4 was enriched for classes 1C-E (89.5% of 1436 patients with baseline magnetic resonance images) compared to unselected populations (e.g., 60.5% of 590 Mayo Clinic patients). The effects of tolvaptan on TKV and eGFR slopes were greater in classes 1C to E than in 1B. In TEMPO 3:4, tolvaptan reduced TKV and eGFR slopes from 5.51% to 2.80% per year and from −3.70 to −2.78 ml/min/1.73 m² per year, and lowered the risk for a composite endpoint of clinical progression events (hazard ratio=0.87). Restricting enrollment to classes 1C to E would have reduced TKV and eGFR slopes from 5.78% to 2.91% per year and from −3.93 to −2.82 ml/min/1.73 m² per year, and the risk of the composite endpoint (hazard ratio=0.84, P=0.003), with 10.5% fewer patients.

In another study [5], a post hoc analysis of the early disease HALT-PKD study, an RCT that studied the effect of rigorous versus standard BP control on rates of TKV increase and eGFR decline in ADPKD patients with eGFR>60 mL/min/1.73 m², was performed to investigate whether using the classification described above would have increased the power to detect a beneficial treatment effect of rigorous blood pressure (BP) control.

Five hundred and fifty-one patients were classified by two observers (98.2% agreement) into Class 1A (6.2%), 1B (20.3%), 1C (34.1%), 1D (22.1%), 1E (11.8%) and 2 (5.4%). The TKV increase and eGFR decline became steeper from Class 1A through 1E. Rigorous BP control had been shown to be associated with slower TKV increase, without a significant overall effect on the rate of eGFR decline (faster in the first 4 months and marginally slower thereafter). Merging Classes 1A and 2 (lowest severity), 1B and 1C (intermediate severity) and 1D and 1E (highest severity) detected stronger beneficial effects on TKV increase and eGFR decline in Class 1D and E with a smaller number of patients.

SUMMARY OF THE INVENTION

The present invention provides technology that uses an imaging classification of ADPKD to select the most appropriate patients for clinical trials and identify patients with progressive disease likely to benefit from an effective medication or therapy. Briefly, this classification consists of the application of computed tomography (CT) and magnetic resonance (MR) images to assign patients as class 1 (typical, bilateral diffuse presentation, ~95% of the ADPKD population) or class 2 (atypical, asymmetric cyst distribution, ~5% of the ADPKD population) based on prespecified imaging findings. Within class 1, further stratification into A, B, C, D and E, based on height adjusted TKV (HtTKV) and age, showed that the rate of estimated GFR (eGFR) decline and renal survival were significantly different among them, with patients in class C, D and E with rapid to very rapid disease progression and greater eGFR decline. Class 2 includes patients that present with unilateral, segmental, asymmetric, or bilateral atypical presentation (Class 2A), but also patients that present with bilateral distribution with acquired unilateral atrophy or bilateral kidney atrophy (Class 2B). Patients qualifying as class 2A presented low risk for eGFR decline and patients classified as 2B may not benefit from therapies directed to slowing kidney growth. Therefore, the classification is particularly important as it may help to identify patients likely to benefit from an effective therapy. For prognostic enrichment design in randomized clinical trials, it is proposed to exclude class 1A, 1B and 2.

In one embodiment, an apparatus for classifying a patient that has been previously diagnosed to have autosomal dominant polycystic kidney disease (ADPKD) comprises: an input/output interface; a memory; and one or more processors communicably coupled to the input/output interface and the memory, wherein the one or more processors receive a total kidney volume (TKV), a patient height, and a patient age for the patient via the input/output interface, determine a height adjusted TKV (HtTKV) based on the total kidney volume and the patient height, determine an ADPKD classification for the patient based on the height adjusted TKV and the patient age, and provide the ADPKD classification for the patient via the input/output interface. In one aspect, the one or more processors further receive a serum creatinine, a race, a gender, and a future time via the input/output interface, determine a current eGFR based on the serum creatinine, the patient age, the patient race and the patient gender, determine a future eGFR based on the current eGFR, the ADPKD classification and the future time, and provide the current eGFR and the future eGFR for the patient via the input/output interface. In another aspect, the future eGFR is calculated using:

Future eGFR=21.18−1.26*(1 if the patient is female,0 if is male)−0.26*(age at TKV)+0.90*(eGFR at TKV)+0.58*(1 if it is class 1B,0 otherwise)−1.14*(1 if patient is class 1C,0 otherwise)−1.93*(1 if patient is class 1D,0 otherwise)−6.26*(1 if patient is class 1E,0 otherwise)−0.23*(years from TKV)+0.19*(1 if the patient is female,0 if is male)*(years from TKV)−0.02*(age at KV)*(years from TKV)+
0.001*(eGFR at TKV)*(years from TKV)−
1.33*(1 if it is class 1B,0 otherwise)*(years
from TKV)−2.63*(1 if patient is class 1C,0 oth-
erwise)*(years from TKV)−3.48*(1 if patient is
class 1D,0 otherwise)*(years from TKV)−
4.78*(1 if patient is class 1E,0 otherwise)*
(years from TKV), where: age at TKV=patient's age;
eGFR at TKV=current eGFR; and
years from TKV=future time in years.

In another aspect, the one or more processors further receive a first sagittal length, a first coronal length, a first width and a first depth for a first kidney for the patient via the input/output interface, receive a second sagittal length, a second coronal length, a second width and a second depth for a second kidney for the patient via the input/output interface, determine a first kidney volume for the first kidney based on the first sagittal length, the first coronal length, the first width and the first depth, determine a second kidney volume for the second kidney based on the second sagittal length, the second coronal length, the second width and the second depth, determine the TKV for the patient based on the first kidney volume and the second kidney volume, and provide the TKV for the patient via the input/output interface. In another aspect, the TKV is determined using an ellipsoid equation.

In another aspect, the computing device is integrated into or communicably coupled to a computed tomography (CT) scanner or a magnetic resonance (MR) scanner; and the CT scanner or MR scanner automatically determines and provides the first sagittal length, the first coronal length, the first width and the first depth for the first kidney for the patient and the second sagittal length, the second coronal length, the second width and the second depth for the second kidney for the patient to the computing device. In another aspect, the input/output interface comprises a remote device, and the remote device is communicably coupled to the one or more processors via one or more networks. In another aspect, the computing device is integrated into or communicably coupled to a computed tomography (CT) scanner or a magnetic resonance (MR) scanner; the CT scanner or MR scanner automatically determines and provides the total kidney volume, the patient height, the patient age for the patient to the computing device; and the computing device automatically provides the ADPKD classification for the patient to the CT scanner or MR scanner.

In another aspect, the ADPKD classification estimates a severity of the ADPKD. In another aspect, the ADPKD classification comprises a first classification of typical, bilateral diffuse presentation (class 1), and a second classification of atypical, asymmetric cyst distribution (class 2). In another aspect, the first classification further comprises two or more subclassifications based on whether or not the patient is identified as being likely to benefit from studies, medicines or therapies directed to slowing kidney growth. In another aspect, the first classification further comprises a first subclassification having a slow progressive disease, a second subclassification having an intermediate progressive disease, a third subclassification having a rapid progressive disease, a fourth subclassification having a very rapid progressive disease, and a most rapid progressive disease. In another aspect, the first classification further comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E). In another aspect, the method further comprises providing a recommendation to select or exclude the patient for a clinical trial based on the ADPKD classification. In another aspect, the method further comprises providing a recommendation to select or exclude a medication for the patient based on the ADPKD classification. In another aspect, the method further comprises providing a recommendation to select or exclude a therapy for the patient based on the ADPKD classification. In another aspect, the computing device comprises a server computer, a workstation computer, a laptop computer, a mobile communications device, a personal data assistant, or a medical scanning device.

In another embodiment, a computerized method of classifying a patient that has been previously diagnosed to have autosomal dominant polycystic kidney disease (ADPKD) comprises: providing a computing device having an input/output interface, one or more processors and a memory; receiving a total kidney volume (TKV), a patient height, and a patient age for the patient via the input/output interface; determining a height adjusted TKV (HtTKV) based on the total kidney volume and the patient height using the one or more processors; determining an ADPKD classification for the patient based on the height adjusted TKV and the patient age using the one or more processors; and providing the ADPKD classification for the patient via the input/output interface. In one aspect, the method further comprises: receiving a serum creatinine, a race, a gender, and a future time via the input/output interface; determining a current eGFR based on the serum creatinine, the patient age, the patient race and the patient gender using the one or more processors; determining a future eGFR based on the current eGFR, the ADPKD classification and the future time using the one or more processors; and providing the current eGFR and the future eGFR for the patient via the input/output interface. In another aspect, the future eGFR is calculated using:

Future eGFR=21.18−1.26*(1 if the patient is
female,0 if is male)−0.26*(age at TKV)+0.90*
(eGFR at TKV)+0.58*(1 if it is class 1B,0 oth-
erwise)−1.14*(1 if patient is class 1C,0 other-
wise)−1.93*(1 if patient is class 1D,0
otherwise)−6.26*(1 if patient is class 1E,0 oth-
erwise)−0.23*(years from TKV)+0.19*(1 if the
patient is female,0 if is male)*(years from
TKV)−0.02*(age at KV)*(years from TKV)+
0.001*(eGFR at TKV)*(years from TKV)−
1.33*(1 if it is class 1B,0 otherwise)*(years
from TKV)−2.63*(1 if patient is class 1C,0 oth-
erwise)*(years from TKV)−3.48*(1 if patient is
class 1D,0 otherwise)*(years from TKV)−
4.78*(1 if patient is class 1E,0 otherwise)*
(years from TKV), where: age at TKV=patient's age;
eGFR at TKV=current eGFR; and
years from TKV=future time in years.

In yet another aspect, the method further comprises: receiving a first sagittal length, a first coronal length, a first width and a first depth for a first kidney for the patient via the input/output interface; receiving a second sagittal length, a second coronal length, a second width and a second depth for a second kidney for the patient via the input/output interface; determining a first kidney volume for the first kidney based on the first sagittal length, the first coronal length, the first width and the first depth using the one or more processors; determining a second kidney volume for the second kidney based on the second sagittal length, the second coronal length, the second width and the second depth using the one or more processors; determining the TKV for the patient based on the first kidney volume and the second kidney volume; and providing the TKV for the patient via the input/output interface. In another aspect, the TKV is determined using an ellipsoid equation.

In another aspect, the computing device is integrated into or communicably coupled to a computed tomography (CT) scanner or a magnetic resonance (MR) scanner; and the CT scanner or MR scanner automatically determines and provides the first sagittal length, the first coronal length, the first width and the first depth for the first kidney for the patient and the second sagittal length, the second coronal length, the second width and the second depth for the second kidney for the patient to the computing device. In another aspect, the input/output interface comprises a remote device, and the remote device is communicably coupled to the one or more processors via one or more networks. In another aspect, the computing device is integrated into or communicably coupled to a computed tomography (CT) scanner or a magnetic resonance (MR) scanner; the CT scanner or MR scanner automatically determines and provides the total kidney volume, the patient height, the patient age for the patient to the computing device; and the computing device automatically provides the ADPKD classification for the patient to the CT scanner or MR scanner.

In another aspect, the ADPKD classification estimates a severity of the ADPKD. In another aspect, the ADPKD classification comprises a first classification of typical, bilateral diffuse presentation (class 1), and a second classification of atypical, asymmetric cyst distribution (class 2). In another aspect, the first classification further comprises two or more subclassifications based on whether or not the patient is identified as being likely to benefit from studies, medicines or therapies directed to slowing kidney growth. In another aspect, the first classification further comprises a first subclassification having a slow progressive disease, a second subclassification having an intermediate progressive disease, a third subclassification having a rapid progressive disease, a fourth subclassification having a very rapid progressive disease, and a most rapid progressive disease. In another aspect, the first classification further comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E). In another aspect, the method further comprises providing a recommendation to select or exclude the patient for a clinical trial based on the ADPKD classification. In another aspect, the method further comprises providing a recommendation to select or exclude a medication for the patient based on the ADPKD classification. In another aspect, the method further comprises providing a recommendation to select or exclude a therapy for the patient based on the ADPKD classification. In another aspect, the computing device comprises a server computer, a workstation computer, a laptop computer, a mobile communications device, a personal data assistant, or a medical scanning device. Moreover, the method can be implemented using a non-transitory computer readable medium that when executed causes the one or more processors to perform the method.

BRIEF DESCRIPTION OF THE DRAWINGS

For a more complete understanding of the features and advantages of the present invention, reference is now made to the detailed description of the invention along with the accompanying figures and in which:

FIGS. 4A-4D are images of an input/output screen depicting an example using the apparatus and method of the present invention.

DETAILED DESCRIPTION OF THE INVENTION

Figure 1:
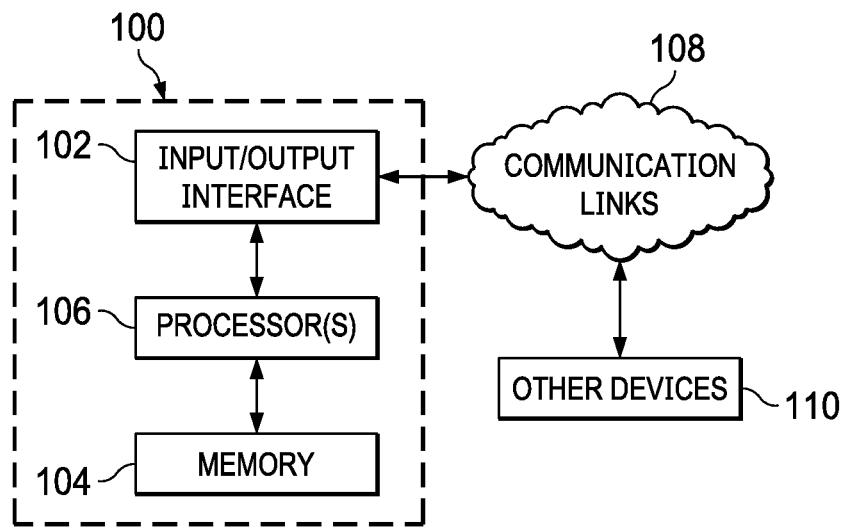
FIG. 1 illustrates a block diagram of an apparatus in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

To overcome some of the limitations of total kidney volume (TKV) as it relates to autosomal dominant polycystic kidney disease (ADPKD), the present invention uses an imaging classification of ADPKD to select the most appropriate patients for clinical trials and identify patients with progressive disease likely to benefit from an effective medication or therapy. Briefly, this classification consists of the application of computed tomography (CT) and magnetic resonance (MR) images to assign patients as class 1 (typical, bilateral diffuse presentation, ~95% of the ADPKD population) or class 2 (atypical, asymmetric cyst distribution, ~5% of the ADPKD population) based on prespecified imaging findings. Within class 1, further stratification into A, B, C, D and E, based on height adjusted TKV (HtTKV) and age, showed that the rate of estimated GFR (eGFR) decline and renal survival were significantly different among them, with patients in class C, D and E with rapid to very rapid disease progression and greater eGFR decline. Class 2 includes patients that present with unilateral, segmental, asymmetric, or bilateral atypical presentation (Class 2A), but also patients that present with bilateral distribution with acquired unilateral atrophy or bilateral kidney atrophy (Class 2B). Patients qualifying as class 2A presented low risk for eGFR decline and patients classified as 2B may not benefit from therapies directed to slowing kidney growth. For prognostic enrichment design in randomized clinical trials, it is proposed to exclude class 1A and 2 and to follow class 1B patients to more precisely define their risk for progression. Therefore, the classification is particularly important as it may help to identify patients likely to benefit from an effective therapy. Indeed, several countries, including Japan, Canada, The Netherlands, and Belgium have already adopted classifications for selecting which patients with ADPKD to treat.

The ellipsoid equation ($\pi/6 \times L \times W \times D$) has been validated for use to estimate TKV from CT or MRI for the purpose of using the classification. The measurements required for the ellipsoid equation and the application of the ellipsoid equation takes less than 5 minutes compared to ~45 minutes that takes to estimate TKV using the gold standard techniques. Furthermore, these measurements can be easily taken by any Nephrologist in their office using electronic CT or MRI files.

The next step is to acknowledge the existence of two different populations of ADPKD patients; patients that present with bilateral and diffuse distribution of the disease (typical or class 1) where all cyst contribute similarly to TKV, and the patients that present with asymmetric, unilateral or loop sided distribution of the disease (atypical or class 2) where there is a normal contralateral kidney or only a few cysts may contribute to a large TKV. This is important because in the patients with atypical presentation TKV is not a good predictor of eGFR decline as there is a contralateral normal kidney or a high TKV may be due only to a few large cysts with large preservation of normal kidney tissue surrounding them.

After this distinction has been made, the classification further stratifies typical patients assuming different rates of TKV increase. The idea behind this distinction is that a TKV of 1500 ml should not be regarded the same in a 20 year old patient or in a 45 year old patient. In order for a patient to have a TKV of 1500 ml at 20 years, this patient has to have a higher rate of TKV increase compared to the patient that achieved the same volume in a longer period of time. Using specific cut off of certain TKV volumes for a specific age, and assuming 5 different TKV grow rates, when then further classify class 1 patients into 1A, 1B, 1C, 1D and 1E, where 1A are the patients with milder disease. It was found that when applying this criterion the different rates of eGFR decline could be detected.

Finally, an algorithm in accordance with the present invention allows the classification of hundreds of patients into 1A, 1B, 1C, 1D or 1E at a time. This algorithm has been developed to facilitate the classification system described above. The current eGFR can be calculated using the Chronic Kidney Disease Epidemiology Collaboration equation [3]. The equation for determining the future eGFR derived from the model is:

Future eGFR=21.18−1.26*(1 if the patient is female,0 if is male)−0.26*(age at TKV)+0.90*(eGFR at TKV)+0.58*(1 if it is class 1B,0 otherwise)−1.14*(1 if patient is class 1C,0 otherwise)−1.93*(1 if patient is class 1D,0 otherwise)−6.26*(1 if patient is class 1E,0 otherwise)−0.23*(years from TKV)+0.19*(1 if the patient is female,0 if is male)*(years from TKV)−0.02*(age at KV)*(years from TKV)+0.001*(eGFR at TKV)*(years from TKV)−1.33*(1 if it is class 1B,0 otherwise)*(years from TKV)−2.63*(1 if patient is class 1C,0 otherwise)*(years from TKV)−3.48*(1 if patient is class 1D,0 otherwise)*(years from TKV)−4.78*(1 if patient is class 1E,0 otherwise)*(years from TKV), where: age at TKV=patient's age;
eGFR at TKV=current eGFR; and
years from TKV=future time in years.

Various embodiments of the present invention will now be described. These embodiments are merely examples and are not intended to limit the scope of the invention.

Now referring to FIG. 1, an apparatus 100 for classifying a patient that has been previously diagnosed to have autosomal dominant polycystic kidney disease (ADPKD) in accordance with the present invention is shown. The apparatus 100 can be a server computer, a workstation computer, a laptop computer, a mobile communications device, a personal data assistant, a medical scanning device or any other device capable of performing the functions described herein. The apparatus 100 includes an input/output interface 102, a memory 104, and one or more processors 106 communicably coupled to the input/output interface 102 and the memory 104. Note that the apparatus 100 may include other components not specifically described herein. The memory 104 can be local, remote or distributed. Likewise, the one or more processors 106 can be local, remote or distributed. The input/output interface 102 can be any mechanism for facilitating the input and/or output of information (e.g., web-based interface, touchscreen, keyboard, mouse, display, printer, etc.) Moreover, the input/output interface 102 can be a remote device communicably coupled to the one or more processors 106 via one or more communication links 108 (e.g., network(s), cable(s), wireless, satellite, etc.). The one or more communication links 108 can communicably couple the apparatus 100 to other devices 110 (e.g., databases, remote devices, hospitals, doctors, researchers, patients, etc.).

The one or more processors 106 receive a total kidney volume (TKV), a patient height, and a patient age for the patient via the input/output interface 102, determine a height adjusted TKV (HtTKV) based on the total kidney volume and the patient height, determine an ADPKD classification for the patient based on the height adjusted TKV and the patient age, and provide the ADPKD classification for the patient via the input/output interface 102. Note that the ADPKD classification can be stored in the memory 104 for later retrieval or use.

In some embodiments, the one or more processors 106 receive a serum creatinine, a race, a gender, and a future time via the input/output interface 102, determine a current eGFR based on the serum creatinine, the patient age, the patient race and the patient gender, determine a future eGFR based on the current eGFR, the ADPKD classification and the future time, and provide the current eGFR and the future eGFR for the patient via the input/output interface 102. Note that the current eGFR and the future eGFR can be stored in the memory 104 for later retrieval or use.

The current eGFR can be calculated using the Chronic Kidney Disease Epidemiology Collaboration equation [3]. The CKD-EPI creatinine equation is based on the same four variables as the MDRD Study equation, but uses a 2-slope spline to model the relationship between estimated GFR and serum creatinine, and a different relationship for age, sex and race. The equation was reported to perform better and with less bias than the MDRD Study equation, especially in patients with higher GFR. This results in reduced misclassification of CKD. As of November 2009, very few clinical laboratories report the estimated GFR using the CKD-EPI creatinine equation. In the future, other GFR estimating equations may outperform CKD-EPI. The CKD-EPI creatinine equation is:

$$GFR=141 \times \min(Scr/\kappa,1)^{\alpha} \times \max(Scr/\kappa,1)^{-1.209} \times 0.993^{Age} \times 1.018[\text{if female}] \times 1.159[\text{if black}]$$

$\kappa$=0.7 if female
$\kappa$=0.9 if male
$\alpha$=−0.329 if female
$\alpha$=−0.411 if male min=The minimum of Scr/κ or 1
max=The maximum of Scr/κ or 1
Scr=serum creatinine (mg/dL)
The future eGFR can be calculated using:

$$\begin{aligned}\text{Future eGFR} =&\, 21.18-1.26*(1 \text{ if the patient is female}, 0 \text{ if is male})-0.26*(\text{age at TKV})+0.90*(\text{eGFR at TKV})+0.58*(1 \text{ if it is class 1B}, 0 \text{ otherwise})-1.14*(1 \text{ if patient is class 1C}, 0 \text{ otherwise})-1.93*(1 \text{ if patient is class 1D}, 0 \text{ otherwise})-6.26*(1 \text{ if patient is class 1E}, 0 \text{ otherwise})-0.23*(\text{years from TKV})+0.19*(1 \text{ if the patient is female}, 0 \text{ if is male})*(\text{years from TKV})-0.02*(\text{age at KV})*(\text{years from TKV})+0.001*(\text{eGFR at TKV})*(\text{years from TKV})-1.33*(1 \text{ if it is class 1B}, 0 \text{ otherwise})*(\text{years from TKV})-2.63*(1 \text{ if patient is class 1C}, 0 \text{ otherwise})*(\text{years from TKV})-3.48*(1 \text{ if patient is class 1D}, 0 \text{ otherwise})*(\text{years from TKV})-4.78*(1 \text{ if patient is class 1E}, 0 \text{ otherwise})*(\text{years from TKV}),\end{aligned}$$

where: age at TKV=patient's age;
eGFR at TKV=current eGFR; and
years from TKV=future time in years.

In some embodiments, the one or more processors 106 receive a first sagittal length, a first coronal length, a first width and a first depth for a first kidney for the patient via the input/output interface 102, receive a second sagittal length, a second coronal length, a second width and a second depth for a second kidney for the patient via the input/output interface 102, determine a first kidney volume for the first kidney based on the first sagittal length, the first coronal length, the first width and the first depth, determine a second kidney volume for the second kidney based on the second sagittal length, the second coronal length, the second width and the second depth, determine the TKV for the patient based on the first kidney volume and the second kidney volume, and provide the TKV for the patient via the input/output interface 102. Typically, an average of the sagittal and coronal lengths will be used to determine the kidney volume. Note that the TKV can be stored in the memory 104 for later retrieval or use. The TKV can be determined using an ellipsoid equation, such as $\pi/6 \times L \times W \times D$.

In some embodiments, the apparatus 100 is integrated into or communicably coupled to a computed tomography (CT) scanner, a magnetic resonance (MR) scanner or other suitable scanner or medical device. In such case, the scanner or medical device automatically determines and provides the first sagittal length, the first coronal length, the first width and the first depth for the first kidney for the patient and the second sagittal length, the second coronal length, the second width and the second depth for the second kidney for the patient to the computing device. Typically, an average of the sagittal and coronal lengths will be used to determine the kidney volume. Likewise, the scanner or medical device can automatically determine and provide the total kidney volume, the patient height, the patient age for the patient to the computing device. The computing device can then automatically provide the ADPKD classification for the patient to the scanner or medical device.

As previously described, the ADPKD classification can estimate a severity of the ADPKD. For example, the ADPKD classification can comprise a first classification of typical, bilateral diffuse presentation (class 1), and a second classification of atypical, asymmetric cyst distribution (class 2). In addition, the first classification can comprise two or more subclassifications based on whether or not the patient is identified as being likely to benefit from studies, medicines or therapies directed to slowing kidney growth. For example, the first classification can comprise a first subclassification having a slow progressive disease, a second subclassification having an intermediate progressive disease, a third subclassification having a rapid progressive disease, a fourth subclassification having a very rapid progressive disease, and a most rapid progressive disease. In another example, the first classification can comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E).

In some embodiments, the one or more processors 106 further provide a recommendation to select or exclude: (a) the patient for a clinical trial based on the ADPKD classification; (b) a medication for the patient based on the ADPKD classification; and/or (c) a therapy for the patient based on the ADPKD classification. The present invention may also use the ADPKD classification for other purposes and action(s)/inaction(s) as will be appreciated by those skilled in the art.

Figure 2A:
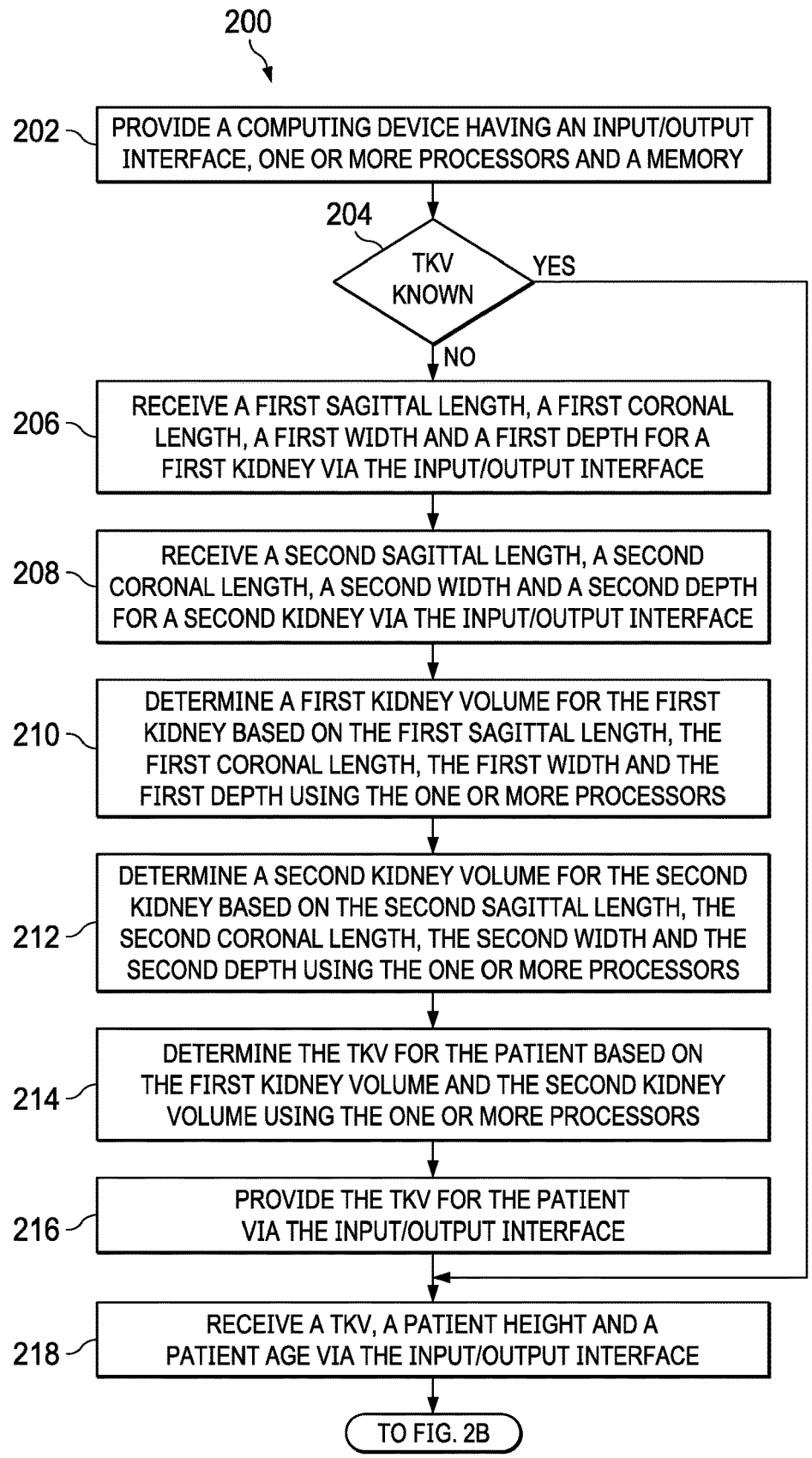
FIGS. 2A-2B illustrates a block diagram of a method in accordance with one embodiment of the present invention.
Figure 2B:
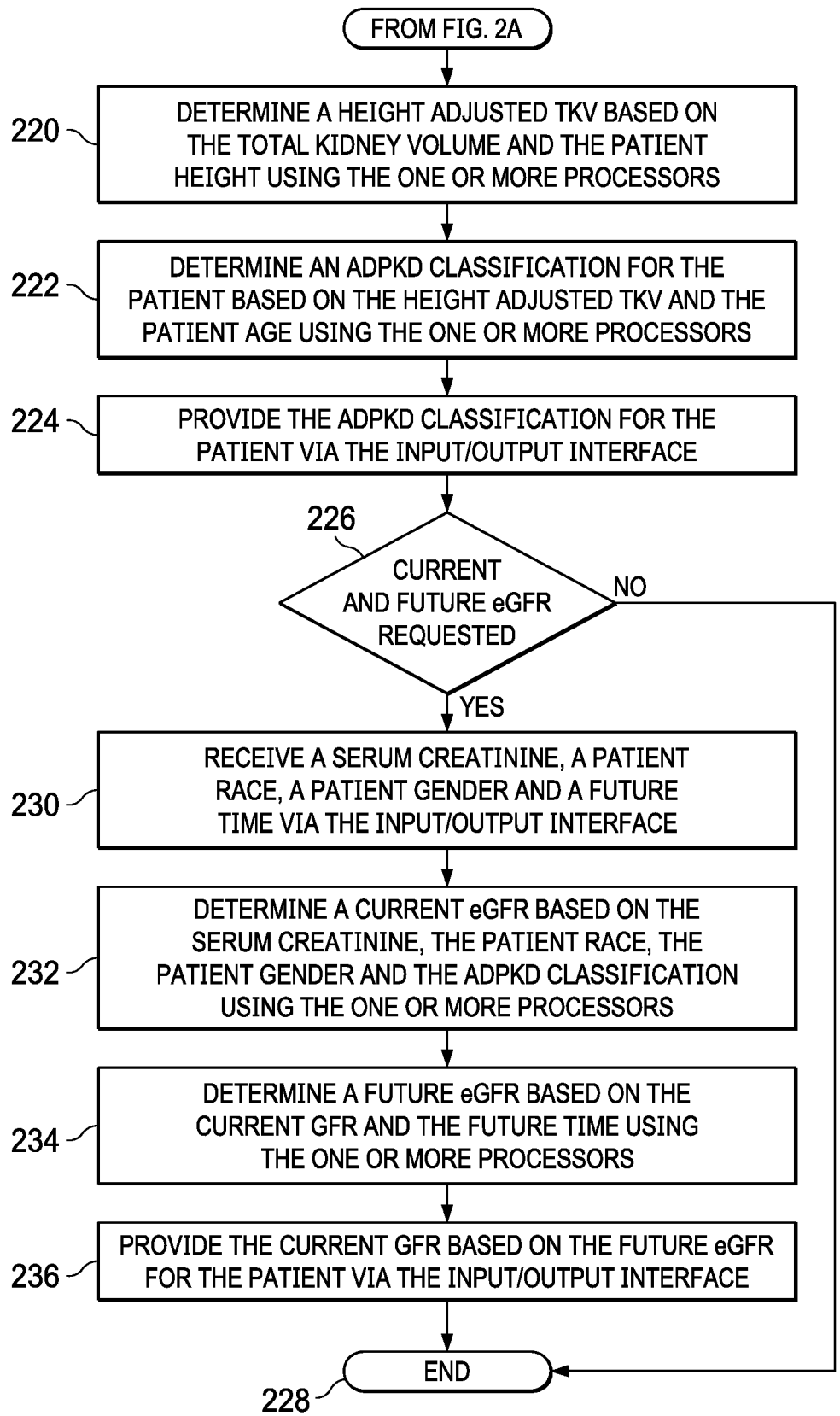
Figure 3A:
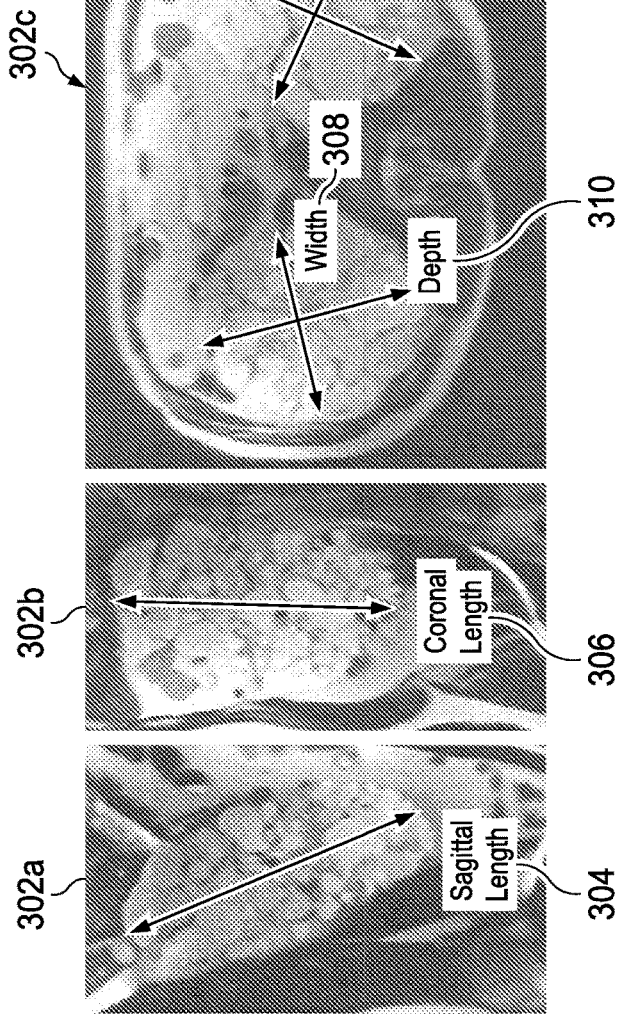
Figure 3B:
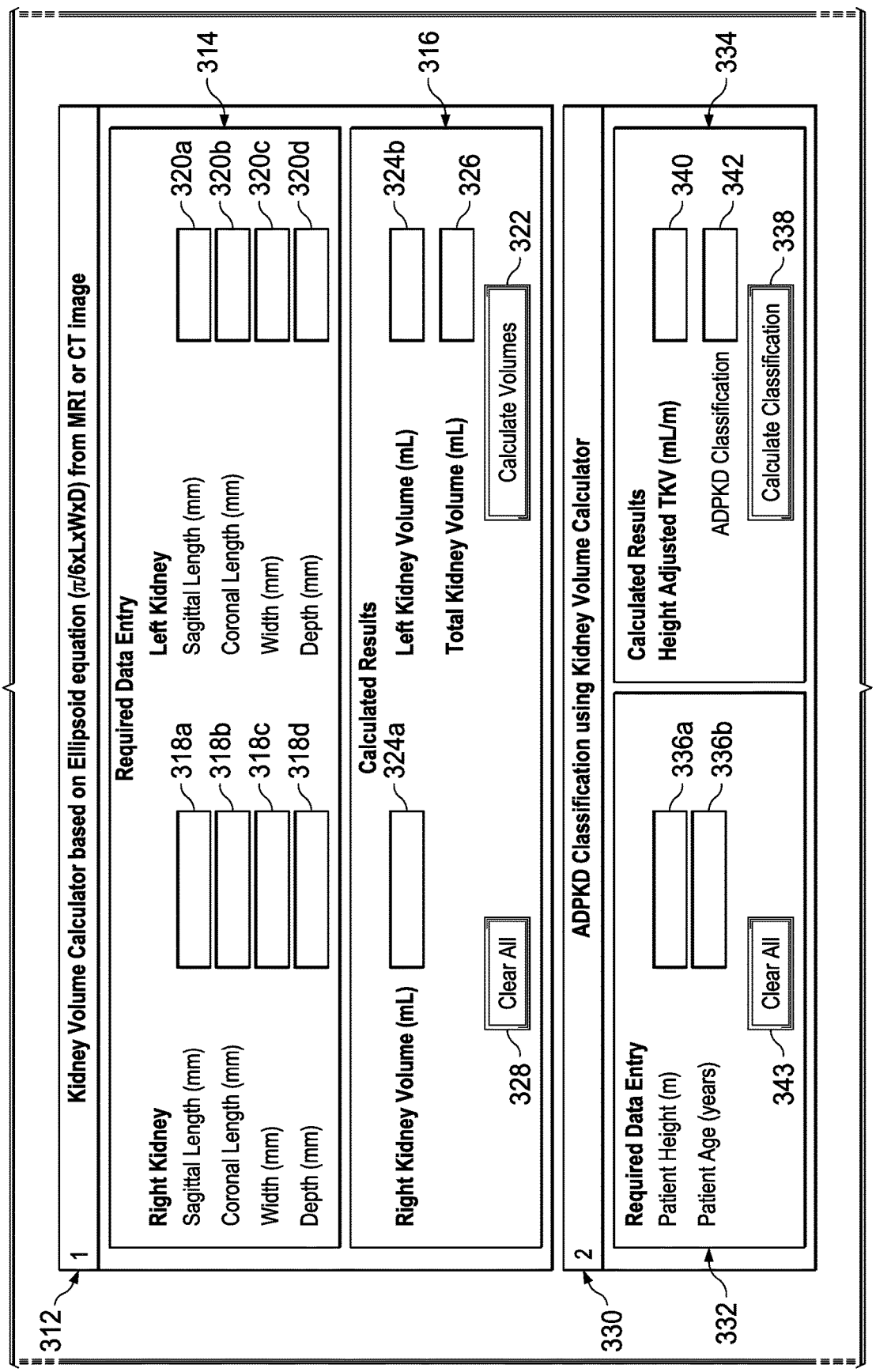
Figure 3C:
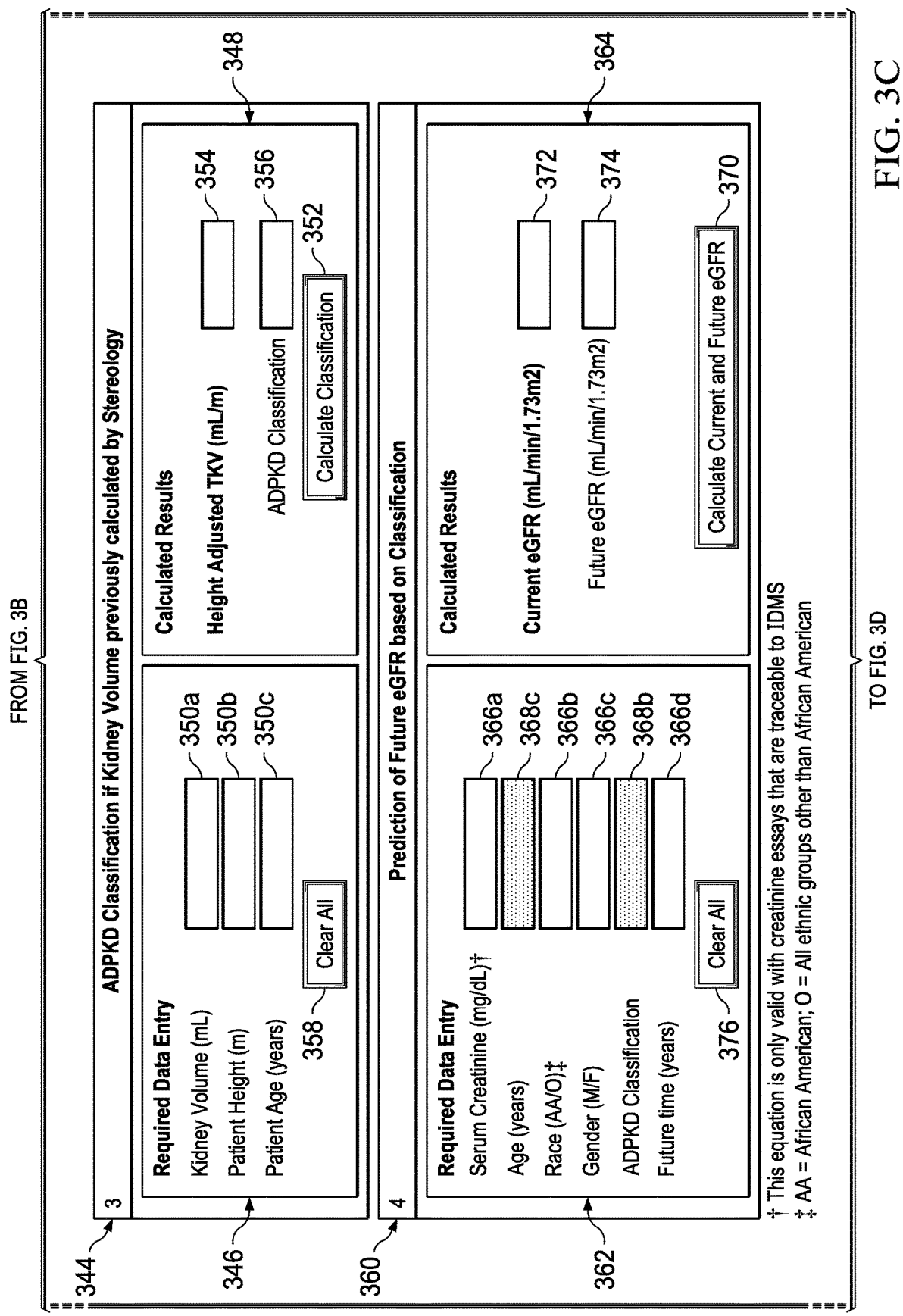
Figure 3D:
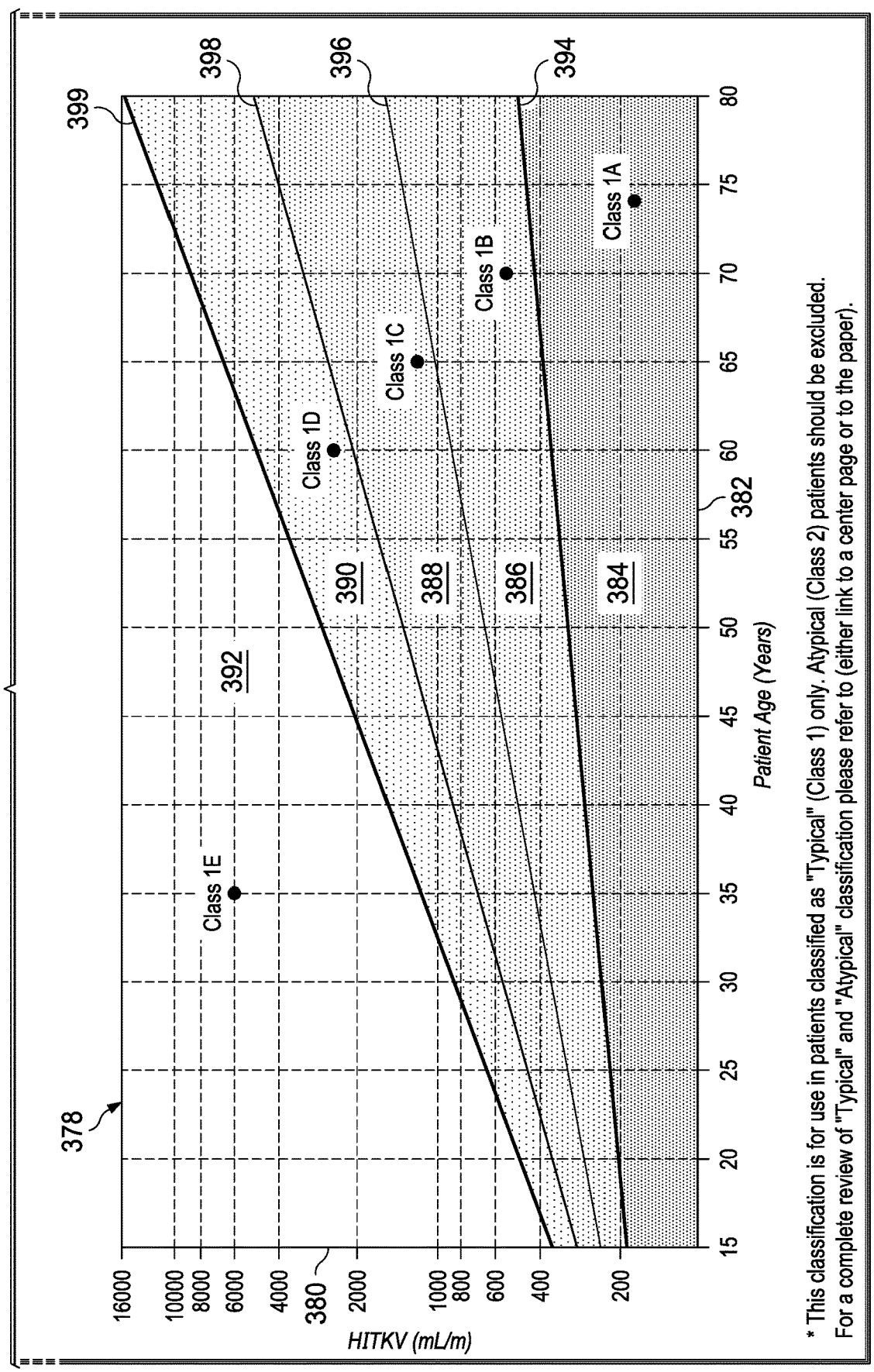

Referring now to FIGS. 2A-2B, a block diagram of a computerized method 200 for classifying a patient that has been previously diagnosed to have ADPKD in accordance with one embodiment of the present invention is shown. A computing device (e.g., apparatus 100) having an input/output interface, one or more processors and a memory is provided in block 202. If the TKV for the patient is not known, as determined in decision block 204, a first sagittal length, a first coronal length, a first width and a first depth for a first kidney for the patient are received via the input/output interface in block 206. A second sagittal length, a second coronal length, a second width and a second depth for a second kidney for the patient are received via the input/output interface in block 208. A first kidney volume for the first kidney is determined based on the first sagittal length, the first coronal length, the first width and the first depth using the one or more processors in block 210. A second kidney volume for the second kidney is determined based on the second sagittal length, the second coronal length, the second width and the second depth using the one or more processors in block 212. Typically, an average of the sagittal and coronal lengths will be used to determine the kidney volume. The TKV for the patient is determined based on the first kidney volume and the second kidney volume using the one or more processors in block 214. The TKV for the patient is provided via the input/output interface in block 216. Note that the TKV can be stored in the memory for later retrieval or use.

Thereafter, or if the TKV for the patient is known, as determined in decision block 204, the TKV, a patient height, and a patient age for the patient are received via the input/output interface in block 218. Note that the TKV can be automatically received from the previous calculation in block 214, or manually provided, or provided from other sources. A height adjusted TKV (HtTKV) is determined based on the total kidney volume and the patient height using the one or more processors in block 220. An ADPKD classification for the patient is determined based on the height adjusted TKV and the patient age using the one or more processors in block 222. The ADPKD classification for the patient is provided via the input/output interface in block 224. Note that the ADPKD classification can be stored in the memory for later retrieval or use. If a current eGFR and future eGFR are not requested, as determined in decision block 226, the process ends in block 228.

If, however, a current eGFR and future eGFR are requested, as determined in decision block 226, a serum creatinine, a race, a gender, and a future time are received via the input/output interface in block 230. A current eGFR based on the serum creatinine, the patient age, the patient race and the patient gender are determined using the one or more processors in block 232. A future eGFR based on the current eGFR, the ADPKD classification and the future time are determined using the one or more processors in block 234. The current eGFR and the future eGFR for the patient are provided via the input/output interface in block 236, and the process ends in block 228. Note that the current eGFR and the future eGFR can be stored in the memory for later retrieval or use. In addition, the foregoing method can be automatically repeated to process large number of patent data, either sequentially or in parallel, in a batch process.

The current eGFR can be calculated using the Chronic Kidney Disease Epidemiology Collaboration equation [3]. The CKD-EPI creatinine equation is based on the same four variables as the MDRD Study equation, but uses a 2-slope spline to model the relationship between estimated GFR and serum creatinine, and a different relationship for age, sex and race. The equation was reported to perform better and with less bias than the MDRD Study equation, especially in patients with higher GFR. This results in reduced misclassification of CKD. As of November 2009, very few clinical laboratories report the estimated GFR using the CKD-EPI creatinine equation. In the future, other GFR estimating equations may outperform CKD-EPI. The CKD-EPI creatinine equation is:

$$GFR = 141 \times \min(Scr/\kappa, 1)^\alpha \times \max(Scr/\kappa, 1)^{-1.209} \times 0.993^{Age} \times 1.018[\text{if female}] \times 1.159[\text{if black}]$$

κ=0.7 if female
κ=0.9 if male
α=−0.329 if female
α=−0.411 if male
min=The minimum of Scr/κ or 1
max=The maximum of Scr/κ or 1
Scr=serum creatinine (mg/dL)
The future eGFR can be calculated using:

Future eGFR=21.18−1.26*(1 if the patient is female,0 if is male)−0.26*(age at TKV)+0.90* (eGFR at TKV)+0.58*(1 if it is class 1B,0 otherwise)−1.14*(1 if patient is class 1C,0 otherwise)−1.93*(1 if patient is class 1D,0 otherwise)−6.26*(1 if patient is class 1E,0 otherwise)−0.23*(years from TKV)+0.19*(1 if the patient is female,0 if is male)*(years from TKV)−0.02*(age at KV)*(years from TKV)+ 0.001*(eGFR at TKV)*(years from TKV)− 1.33*(1 if it is class 1B,0 otherwise)*(years from TKV)−2.63*(1 if patient is class 1C,0 otherwise)*(years from TKV)−3.48*(1 if patient is class 1D,0 otherwise)*(years from TKV)− 4.78*(1 if patient is class 1E,0 otherwise)* (years from TKV), where: age at TKV=patient's age;
eGFR at TKV=current eGFR; and
years from TKV=future time in years.

In some embodiments, the computing device is integrated into or communicably coupled to a computed tomography (CT) scanner, a magnetic resonance (MR) scanner or other suitable scanner or medical device. In such case, the scanner or medical device automatically determines and provides the first sagittal length, the first coronal length, the first width and the first depth for the first kidney for the patient and the second sagittal length, the second coronal length, the second width and the second depth for the second kidney for the patient to the computing device. Typically, an average of the sagittal and coronal lengths will be used to determine the kidney volume. Likewise, the scanner or medical device can automatically determine and provide the total kidney volume, the patient height, the patient age for the patient to the computing device. The computing device can then automatically provide the ADPKD classification for the patient to the scanner or medical device.

As previously described, the ADPKD classification can estimate a severity of the ADPKD. For example, the ADPKD classification can comprise a first classification of typical, bilateral diffuse presentation (class 1), and a second classification of atypical, asymmetric cyst distribution (class 2). In addition, the first classification can comprise two or more subclassifications based on whether or not the patient will benefit from studies, medicines or therapies directed to slowing kidney growth. For example, the first classification can comprise a first subclassification having a slow progressive disease, a second subclassification having an intermediate progressive disease, a third subclassification having a rapid progressive disease, a fourth subclassification having a very rapid progressive disease, and a most rapid progressive disease. In another example, the first classification can comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E).

In some embodiments, the one or more processors further provide a recommendation to select or exclude: (a) the patient for a clinical trial based on the ADPKD classification; (b) a medication for the patient based on the ADPKD classification; and/or (c) a therapy for the patient based on the ADPKD classification. The present invention may also use the ADPKD classification for other purposes and action(s)/inaction(s) as will be appreciated by those skilled in the art.

Figure 3:
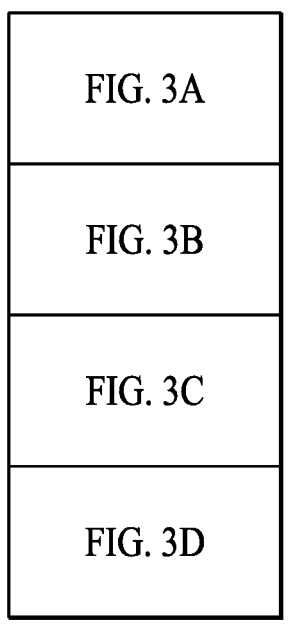
FIG. 3 is an image of an input/output screen in accordance with another embodiment of the present invention.

Moreover, the method 200 can be implemented using a non-transitory computer readable medium that when executed causes the one or more processors to perform the method Now referring to FIG. 3, an image of an input/output screen 300 in accordance with another embodiment of the present invention is shown. The input/output screen 300 includes three images 302a, 302b, 302c that show how the sagittal length 304, coronal length 306, width 308 and depth 310 of the kidneys should be measured. The input/output screen 300 also includes a kidney volume calculator box 312 having an input portion 314 and an output portion 316. The sagittal length, coronal length, width and depth for the right kidney are entered into boxes 318a, 318b, 318c and 318d, respectively, in the input portion 314 of the kidney volume calculator box 312. Similarly, the sagittal length, coronal length, width and depth for the left kidney are entered in to boxes 320a, 320b, 320c and 320d, respectively, in the input portion 314 of the kidney volume calculator box 312. Once this data is entered and the calculate volumes button 322 is clicked or selected, the right kidney volume, the left kidney volume and the total kidney volume are calculated and displayed in boxes 324a, 324b and 326, respectively, in the output portion 316 of the kidney volume calculator box 312.

All the data displayed in the kidney volume calculator box 312 can be cleared by clicking or selecting the clear all button 328.

In addition, the input/output screen 300 includes a first ADPKD classification box 330 having an input portion 332 and an output portion 334. The patient height and patient age are entered into boxes 336*a* and 336*b*, respectively, in the input portion 332 of the first classification box 330. Once this data is entered and the calculate classification button 338 is clicked or selected, the height adjusted TKV and ADPKD classification are calculated and displayed in boxes 340 and 342, respectively, in the output portion 334 of the ADPKD classification box 330. All the data displayed in first ADPKD classification box 330 can be cleared by clicking or selecting the clear all button 340.

If, however, the TKV is already known, a second ADPKD classification box 344 can be used. The second ADPKD classification box 344 has an input portion 346 and an output portion 348. The total kidney volume, patient height and patient age are entered into boxes 350*a*, 350*b* and 350*c*, respectively, in the input portion 346 of the second classification box 344. Once this data is entered and the calculate classification button 352 is clicked or selected, the height adjusted TKV and ADPKD classification are calculated and displayed in boxes 354 and 356, respectively, in the output portion 348 of the second ADPKD classification box 344. All the data displayed in the second ADPKD classification box 344 can be cleared by clicking or selecting the clear all button 358.

Moreover, the input/output screen 300 includes a prediction of future eGFR box 360 having an input portion 362 and an output portion 364. The serum creatinine, race, gender and future time are entered into boxes 366*a*, 366*b*, 366*c* and 366*d*, respectively, in the input portion 362 of the prediction of future eGFR box 364. The age and ADPKD classification are automatically displayed in boxes 368*a* and 368*b*, respectively, in the input portion 362 of the prediction of future eGFR box 360 based on previous entries and calculations. Once this data is entered and the calculate current and future eGFR button 370 is clicked or selected, the current eGFR and future eGFR are calculated and displayed in boxes 372 and 374, respectively in the output portion 364 of the prediction of future eGFR box 360. All the data displayed in the prediction of future eGFR box 360 can be cleared by clicking or selecting the clear all button 376.

The input/output screen 300 also includes an interactive graph 378 showing the various ADPKD classifications based on HtTKV 380 and age 382. The ADPKD classifications are class 1A 384, class 1B 386, class 1C 388, class 1D 390 and class 1E 392. The interactive graph 378 displays the HtTKV 380 and age 382 values when a cursor or pointing device is positioned somewhere in the interactive graph 378. In this example, the classification boundaries (lines) are:

First line 394 separating class 1A 384 and class 1B 386 (Age=15, HtTKV=187.535); (Age=80, HtTKV=493.599)

Second line 396 separating class 1B 386 and class 1C 388 (Age=15, HtTKV=233.695); (Age=80, HtTKV=1576.134)

Third line 398 separating class 1C 388 and class 1D 390 (Age=15, HtTKV=290.292); (Age=80, HtTKV=5074.514)

Fourth line 399 separating class 1D 390 and class 1E 392 (Age=15, HtTKV=359.484); (Age=80, HtTKV=15869.399)

Although this example depicts all the information on a single screen 300, those skilled in the art will recognize that the information can be provided using multiple screens.

Figure 4A:
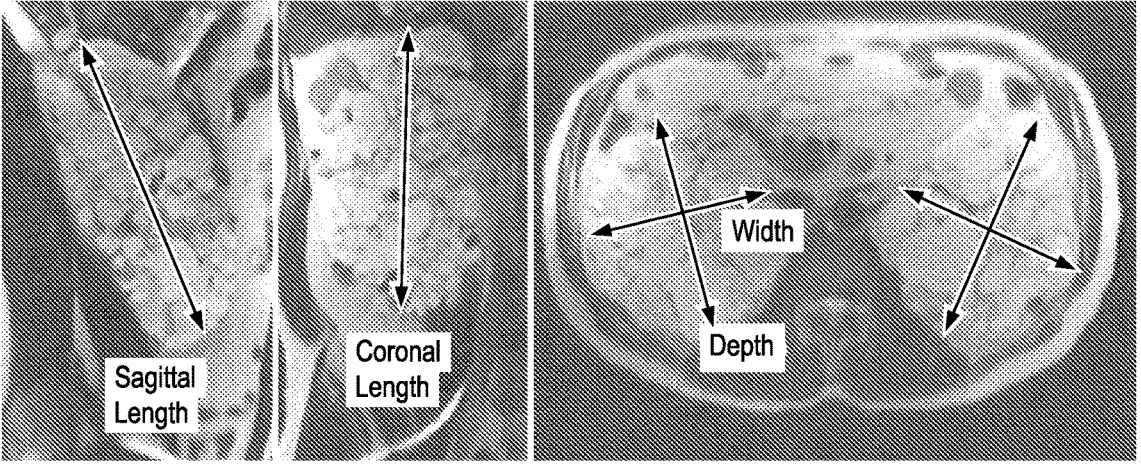

Referring now, to FIGS. 4A-4D, images of input/output screens depicting an example using the apparatus and method of the present invention are shown. The data boxes and buttons have been described above in reference to FIG. 3. As shown in FIG. 4A, the following values are entered in the appropriate data boxes:

| Right Kidney | | Left Kidney | |
|---|---|---|---|
| Sagittal Length (mm) | 155 | Sagittal Length (mm) | 150 |
| Coronal Length (mm) | 165 | Coronal Length (mm) | 160 |
| Width (mm) | 68 | Width (mm) | 65 |
| Depth (mm) | 70 | Depth (mm) | 68 |

Figure 4B:
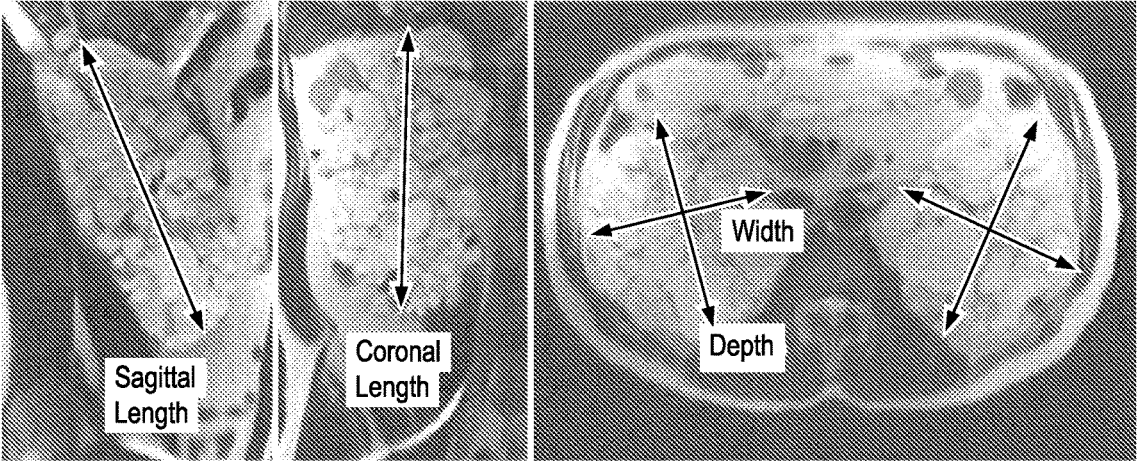

As shown in FIG. 4B, when the calculate volumes button is clicked or selected, the following data is calculated and displayed:

| Right Kidney Volume (mL) | 398.8 | Left Kidney Volume (mL) | 358.7 |
|---|---|---|---|
| | | Total Kidney Volume (mL) | 757.5 |

As shown in FIG. 4A, the following values are entered in the appropriate data boxes:

| Patient Height (m) | 1.7 |
|---|---|
| Patient Age (years) | 25 |

As shown in FIG. 4B, when the calculate classification button is clicked or selected, the following data is calculated and displayed:

| Height Adjusted TKV (mL/m) | 445.6 |
|---|---|
| ADPKD Classification | 1C |

As shown in FIG. 4C, the following values are entered in the appropriate data boxes:

| Kidney Volume (mL) | 757.5 |
|---|---|
| Patient Height (m) | 1.7 |
| Patient Age (years) | 25 |

As shown in FIG. 4D, when the calculate classification button is clicked or selected, the following data is calculated and displayed:

| Height Adjusted TKV (mL/m) | 445.6 |
|---|---|
| ADPKD Classification | 1C |

As shown in FIG. 4C, the following values are entered or automatically populated from other calculations in the appropriate data boxes:

| Seryn Creatinine (mg/dL) | 1.2 |
|---|---|
| Age (years) | 25 |
| Race (AA/O) | O |

| Gender (M/F) | M |
| ADPKD Classification | 1C |
| Future time (years) | 5 |

As shown in FIG. 4D, when the calculate current and future eGFR button is clicked or selected, the following data is calculated and displayed:

| Current eGFR (mL/min/1.73 m$^2$) | 83.5 |
| Future eGFR (mL/min/1.73 m$^2$) | 72.3 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A computerized method of classifying a patient that has been previously diagnosed to have autosomal dominant polycystic kidney disease (ADPKD) comprising:
providing a computing device having an input/output interface, one or more processors and a memory;
receiving a total kidney volume (TKV), a patient height, and a patient age for the patient via the input/output interface;
determining a height adjusted TKV (HtTKV) based on the total kidney volume and the patient height using the one or more processors;
determining an ADPKD classification for the patient based on the height adjusted TKV and the patient age using the one or more processors;
providing the ADPKD classification for the patient via the input/output interface; and
selecting or excluding a medication, a therapy or a clinical trial to treat the patient based on the ADPKD classification.

2. The method of claim 1, further comprising:
receiving a serum creatinine, a race, a gender, and a future time via the input/output interface;
determining a current eGFR based on the serum creatinine, the patient age and, the patient race and the patient gender using the one or more processors;
determining a future eGFR based on the current eGFR, the ADPKD classification and the future time using the one or more processors; and
providing the current eGFR and the future eGFR for the patient via the input/output interface.

3. The method of claim 2, wherein the future eGFR is determined using:

Future eGFR=21.18−1.26*(1 if the patient is female,0 if is male)−0.26*(age at TKV)+0.90*(eGFR at TKV)+0.58*(1 if it is class 1B,0 otherwise)−1.14*(1 if patient is class 1C,0 otherwise)−1.93*(1 if patient is class 1D,0 otherwise)−6.26*(1 if patient is class 1E,0 otherwise)−0.23*(years from TKV)+0.19*(1 if the patient is female,0 if is male)*(years from TKV)−0.02*(age at KV)*(years from TKV)+0.001*(eGFR at TKV)*(years from TKV)−1.33*(1 if it is class 1B,0 otherwise)*(years from TKV)−2.63*(1 if patient is class 1C,0 otherwise)*(years from TKV)−3.48*(1 if patient is class 1D,0 otherwise)*(years from TKV)−4.78*(1 if patient is class 1E,0 otherwise)*(years from TKV), where: age at TKV=patient's age;
eGFR at TKV=current eGFR; and
years from TKV=future time in years.

4. The method of claim 1, further comprising:
receiving a first sagittal length, a first coronal length, a first width and a first depth for a first kidney for the patient via the input/output interface;
receiving a second sagittal length, a second coronal length, a second width and a second depth for a second kidney for the patient via the input/output interface;
determining a first kidney volume for the first kidney based on the first sagittal length, the first coronal length, the first width and the first depth using the one or more processors;
determining a second kidney volume for the second kidney based on the second sagittal length, the second coronal length, the second width and the second depth using the one or more processors;
determining the TKV for the patient based on the first kidney volume and the second kidney volume; and
providing the TKV for the patient via the input/output interface.

5. The method of claim 4, wherein the TKV is determined using an ellipsoid equation.

6. The method of claim 4, wherein:
the computing device is integrated into or communicably coupled to a computed tomography (CT) scanner or a magnetic resonance (MR) scanner; and
the CT scanner or MR scanner automatically determines and provides the first sagittal length, the first coronal length, the first width and the first depth for the first kidney for the patient and the second sagittal length, the second coronal length, the second width and the second depth for the second kidney for the patient to the computing device.

7. The method of claim 1, wherein:
the computing device is integrated into or communicably coupled to a computed tomography (CT) scanner or a magnetic resonance (MR) scanner;
the CT scanner or MR scanner automatically determines and provides the total kidney volume, the patient height, the patient age for the patient to the computing device; and
the computing device automatically provides the ADPKD classification for the patient to the CT scanner or MR scanner.

8. The method of claim 1, wherein the ADPKD classification estimates a severity of the ADPKD.

9. The method of claim 1, wherein the ADPKD classification comprises a first classification of typical, bilateral diffuse presentation (class 1), and a second classification of atypical, asymmetric cyst distribution (class 2).

10. The method of claim 9, wherein the first classification further comprises two or more subclassifications based on whether or not the patient is identified as being likely to benefit from studies, medicines or therapies directed to slowing kidney growth.

11. The method of claim 9, wherein the first classification further comprises a first subclassification having a slow progressive disease, a second subclassification having an intermediate progressive disease, a third subclassification having a rapid progressive disease, a fourth subclassification having a very rapid progressive disease, and a most rapid progressive disease.

12. The method of claim 9, wherein the first classification further comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E).

13. An apparatus for classifying a patient that has been previously diagnosed to have autosomal dominant polycystic kidney disease (ADPKD) comprising:
an input/output interface;
a memory; and
one or more processors communicably coupled to the input/output interface and the memory, wherein the one or more processors receive a total kidney volume (TKV), a patient height, and a patient age for the patient via the input/output interface, determine a height adjusted TKV (HtTKV) based on the total kidney volume and the patient height, determine an ADPKD classification for the patient based on the height adjusted TKV and the patient age, and provide the ADPKD classification for the patient via the input/output interface; and
wherein a medication, a therapy or a clinical trial is selected or excluded to treat the patient based on the ADPKD classification.

14. The apparatus of claim 13, wherein the one or more processors further receive a serum creatinine, a race, a gender, and a future time via the input/output interface, determine a current eGFR based on the serum creatinine, the patient age, the patient race and the patient gender, determine a future eGFR based on the current eGFR, the ADPKD classification and the future time, and provide the current eGFR and the future eGFR for the patient via the input/output interface.

15. The apparatus of claim 14, wherein the future eGFR is determined using:

$$\begin{aligned}\text{Future eGFR} = &21.18 - 1.26*(1 \text{ if the patient is female}, 0 \text{ if is male}) - 0.26*(\text{age at TKV}) + 0.90*(\text{eGFR at TKV}) + 0.58*(1 \text{ if it is class 1B}, 0 \text{ otherwise}) - 1.14*(1 \text{ if patient is class 1C}, 0 \text{ otherwise}) - 1.93*(1 \text{ if patient is class 1D}, 0 \text{ otherwise}) - 6.26*(1 \text{ if patient is class 1E}, 0 \text{ otherwise}) - 0.23*(\text{years from TKV}) + 0.19*(1 \text{ if the patient is female}, 0 \text{ if is male})*(\text{years from TKV}) - 0.02*(\text{age at KV})*(\text{years from TKV}) + 0.001*(\text{eGFR at TKV})*(\text{years from TKV}) - 1.33*(1 \text{ if it is class 1B}, 0 \text{ otherwise})*(\text{years from TKV}) - 2.63*(1 \text{ if patient is class 1C}, 0 \text{ otherwise})*(\text{years from TKV}) - 3.48*(1 \text{ if patient is class 1D}, 0 \text{ otherwise})*(\text{years from TKV}) - 4.78*(1 \text{ if patient is class 1E}, 0 \text{ otherwise})*(\text{years from TKV}),\end{aligned}$$

where: age at TKV=patient's age;
eGFR at TKV=current eGFR; and
years from TKV=future time in years.

16. The apparatus of claim 13, wherein the one or more processors further receive a first sagittal length, a first coronal length, a first width and a first depth for a first kidney for the patient via the input/output interface, receive a second sagittal length, a second coronal length, a second width and a second depth for a second kidney for the patient via the input/output interface, determine a first kidney volume for the first kidney based on the first sagittal length, the first coronal length, the first width and the first depth, determine a second kidney volume for the second kidney based on the second sagittal length, the second coronal length, the second width and the second depth, determine the TKV for the patient based on the first kidney volume and the second kidney volume, and provide the TKV for the patient via the input/output interface.

17. The apparatus of claim 16, wherein:
the apparatus is integrated into or communicably coupled to a computed tomography (CT) scanner or a magnetic resonance (MR) scanner; and
the CT scanner or MR scanner automatically determines and provides the first sagittal length, the first coronal length, the first width and the first depth for the first kidney for the patient and the second sagittal length, the second coronal length, the second width and the second depth for the second kidney for the patient to the computing device.

18. The apparatus of claim 16, wherein the TKV is determined using an ellipsoid equation.

19. The apparatus of claim 13, wherein:
the input/output interface comprises a remote device, and the remote device is communicably coupled to the one or more processors via one or more networks; or
the apparatus comprises a server computer, a workstation computer, a laptop computer, a mobile communications device, a personal data assistant, or a medical scanning device.

20. The apparatus of claim 13, wherein:
the computing device is integrated into or communicably coupled to a computed tomography (CT) scanner or a magnetic resonance (MR) scanner;
the CT scanner or MR scanner automatically determines and provides the total kidney volume, the patient height, the patient age for the patient to the computing device; and
the computing device automatically provides the ADPKD classification for the patient to the CT scanner or MR scanner.

21. The apparatus of claim 13, wherein the ADPKD classification estimates a severity of the ADPKD.

22. The apparatus of claim 13, wherein the ADPKD classification comprises a first classification of typical, bilateral diffuse presentation (class 1), and a second classification of atypical, asymmetric cyst distribution (class 2).

23. The apparatus of claim 22, wherein the first classification further comprises two or more subclassifications based on whether or not the patient is identified as being likely to benefit from studies, medicines or therapies directed to slowing kidney growth.

24. The apparatus of claim 22, wherein the first classification further comprises a first subclassification having a slow progressive disease, a second subclassification having an intermediate progressive disease, a third subclassification having a rapid progressive disease, a fourth subclassification having a very rapid progressive disease, and a most rapid progressive disease.

25. The apparatus of claim 22, wherein the first classification further comprises a first subclassification having an estimated kidney growth rate of less that 1.5% (subclass 1A), a second subclassification having the estimated kidney growth rate of 1.5 to 3.0% (subclass 1B), a third subclassification having the estimated kidney growth rate of 3.0 to 4.5% (subclass 1C), a fourth subclassification having the estimated kidney growth rate of 4.5 to 6.0% (subclass 1D), and a fifth subclassification having the estimated kidney growth rate of greater than 6.0% (subclass 1E).

* * * * *